(12) United States Patent
Tate et al.

(10) Patent No.: US 9,842,729 B2
(45) Date of Patent: Dec. 12, 2017

(54) SYSTEMS AND METHODS FOR USING INTERLEAVING WINDOW WIDTHS IN TANDEM MASS SPECTROMETRY

(71) Applicant: DH Technologies Development Pte. Ltd., Singapore (SG)

(72) Inventors: Stephen A. Tate, Barrie (CA); Ronald F. Bonner, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/259,766

(22) Filed: Sep. 8, 2016

(65) Prior Publication Data

US 2016/0379813 A1 Dec. 29, 2016

Related U.S. Application Data

(63) Continuation of application No. 15/098,200, filed on Apr. 13, 2016, now Pat. No. 9,466,471, which is a (Continued)

(51) Int. Cl.
*H01J 49/40* (2006.01)
*B01D 59/44* (2006.01)
(Continued)

(52) U.S. Cl.
CPC ...... *H01J 49/0045* (2013.01); *G01N 30/7233* (2013.01); *G01N 30/8631* (2013.01);
(Continued)

(58) Field of Classification Search
CPC .............. H01J 49/0036; H01J 49/0009; H01J 49/0031; H01J 49/004; H01J 49/0081;
(Continued)

(56) References Cited

U.S. PATENT DOCUMENTS 4,283,626 A * 8/1981 Siegel ................... H01J 49/004
  250/282
4,472,631 A * 9/1984 Enke ....................... B01D 59/44
  250/281
(Continued)

*Primary Examiner* — David A Vanore
(74) *Attorney, Agent, or Firm* — John R. Kasha; Kelly L. Kasha; Kasha Law LLC

(57) ABSTRACT

Systems and methods are provided for analyzing a sample using overlapping measured mass selection window widths. A mass range of a sample is divided into two or more target mass selection window widths using a processor. The two or more target widths can have the same width or variable widths. A tandem mass spectrometer is instructed to perform two or more fragmentation scans across the mass range using the processor. Each fragmentation scan of the two or more fragmentation scans includes a measured mass selection window width. The two or more measured widths of the two or more fragmentation scans can have the same width or variable widths. At least two of the two or more measured mass selection window widths overlap. The overlap in measured mass selection window widths corresponds to at least one target mass selection window width.

20 Claims, 7 Drawing Sheets

Related U.S. Application Data continuation of application No. 14/922,823, filed on Oct. 26, 2015, now Pat. No. 9,343,282, which is a continuation of application No. 14/401,032, filed as application No. PCT/IB2013/000724 on Apr. 19, 2013, now Pat. No. 9,202,677.

(60) Provisional application No. 61/649,199, filed on May 18, 2012.

(51) Int. Cl.
*H01J 49/00* (2006.01)
*G06F 19/00* (2011.01)
*G01N 30/86* (2006.01)
*G01N 30/72* (2006.01)

(52) U.S. Cl.
CPC .......... *G06F 19/703* (2013.01); *H01J 49/004* (2013.01); *H01J 49/0009* (2013.01); *H01J 49/0031* (2013.01); *H01J 49/0036* (2013.01)

(58) Field of Classification Search
CPC ...... H01J 49/0045; H01J 49/40; B01D 59/44; G01N 30/72; G01N 30/8631; G01N 30/8665
USPC ............... 250/281, 282, 286, 287, 283, 288; 702/23, 85, 22, 26, 2
See application file for complete search history.

(56) References Cited

U.S. PATENT DOCUMENTS

| | | | | |
|---|---|---|---|---|
| 4,507,555 | A * | 3/1985 | Chang | G01N 30/72 250/281 |
| 6,800,846 | B2 * | 10/2004 | Bateman | H01J 49/062 250/281 |
| 7,534,622 | B2 * | 5/2009 | Hunt | G01N 33/6848 436/173 |
| 7,982,181 | B1 * | 7/2011 | Senko | G01N 30/72 250/281 |
| 9,202,677 | B2 * | 12/2015 | Tate | H01J 49/0031 |
| 9,343,282 | B2 * | 5/2016 | Tate | H01J 49/0031 |
| 9,466,471 | B2 * | 10/2016 | Tate | H01J 49/0031 |
| 2006/0169883 | A1 * | 8/2006 | Wang | B01D 59/44 250/282 |
| 2009/0236516 | A1 * | 9/2009 | Kishi | H01J 49/004 250/287 |
| 2014/0158881 | A1 * | 6/2014 | Cooper | H01J 49/0009 250/282 |
| 2014/0252218 | A1 * | 9/2014 | Wright | H01J 49/0031 250/282 |
| 2015/0097113 | A1 * | 4/2015 | Campbell | H01J 49/0031 250/282 |
| 2015/0129757 | A1 * | 5/2015 | Bonner | H01J 49/0031 250/282 |
| 2015/0136968 | A1 * | 5/2015 | Tate | H01J 49/0031 250/282 |

\* cited by examiner

SYSTEMS AND METHODS FOR USING INTERLEAVING WINDOW WIDTHS IN TANDEM MASS SPECTROMETRY

CROSS REFERENCE TO RELATED APPLICATION

This application is a continuation of U.S. patent application Ser. No. 15/098,200, filed Apr. 13, 2016, which is a continuation of U.S. patent application Ser. No. 14/922,823, filed Oct. 26, 2015, now U.S. Pat. No. 9,343,282, which is a continuation of U.S. patent application Ser. No. 14/401,032, filed Nov. 13, 2014, filed as Application No. PCT/IB2013/000724 on Apr. 19, 2013, now U.S. Pat. No. 9,202,677, which claims the benefit of U.S. Provisional Patent Application No. 61/649,199, filed May 18, 2012, the disclosures of which are incorporated by reference herein in their entireties.

INTRODUCTION

Both qualitative and quantitative information can be obtained from a tandem mass spectrometer. In such an instrument a precursor ion is selected in a first mass analyzer, fragmented and the fragments analyzed in a second analyzer or in a second scan of the first analyzer. The fragment ion spectrum can be used to identify the molecule and the intensity of one or more fragments can be used to quantitate the amount of the compound present in a sample.

Selected reaction monitoring (SRM) is a well-known example of this where a precursor ion is selected, fragmented, and passed to a second analyzer which is set to transmit a single ion. A response is generated when a precursor of the selected mass fragments to give an ion of the selected fragment mass, and this output signal can be used for quantitation. The instrument may be set to measure several fragment ions for confirmation purposes or several precursor-fragment combinations to quantitate different compounds.

The sensitivity and specificity of the analysis are affected by the width of the mass window selected in the first mass analysis step. Wide windows transmit more ions giving increased sensitivity, but may also allow ions of different mass to pass; if the latter give fragments at the same mass as the target compound interference will occur and the accuracy will be compromised.

In some mass spectrometers the second mass analyzer can be operated at high resolution, allowing the fragment ion window to be narrow so that the specificity can to a large degree be recovered. These instruments may also detect all fragments so they are inherently detecting different fragments. With such an instrument it is feasible to use a wide window to maximize sensitivity.

These recently developed high-resolution and high-throughput instruments allow a mass range to be accurately scanned within a time interval using multiple scans with adjacent or overlapping mass window widths. The collection of each spectrum at each time interval of the separation is a collection of spectra for the entire mass range. One exemplary method for using windowed mass spectrometry scans to scan an entire mass range is called sequential windowed acquisition (SWATH).

Currently a SWATH user has to balance the number of SWATH experiments, the accumulation time, and also the number of data points across a peak. For example, if the user tries to use narrow mass window widths across a mass range the result may be that there is not enough sensitivity or the cycle time is too large to provide sufficient data points across a peak.

BRIEF DESCRIPTION OF THE DRAWINGS

The skilled artisan will understand that the drawings, described below, are for illustration purposes only. The drawings are not intended to limit the scope of the present teachings in any way.

Figure 1:
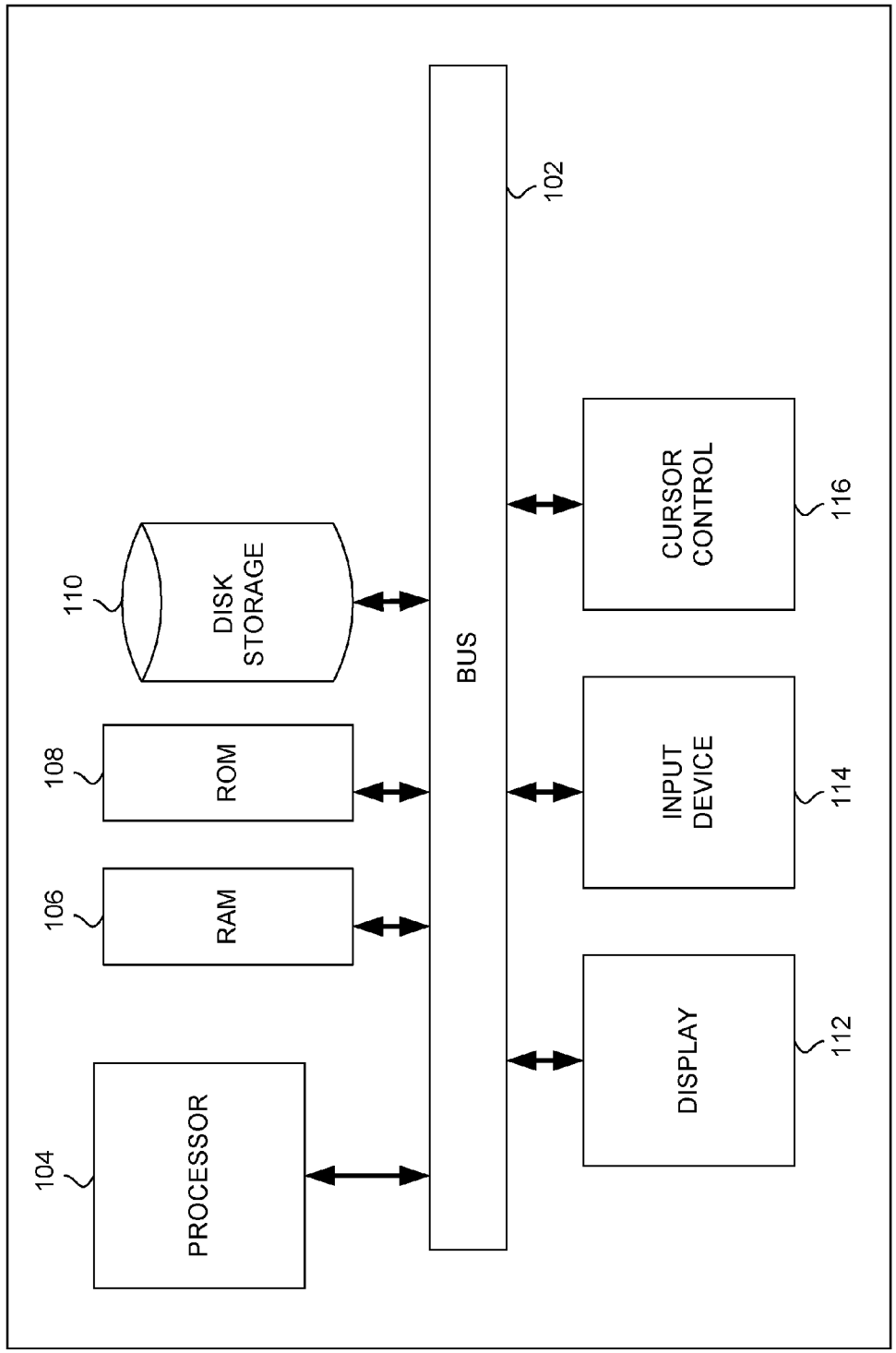
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods of Data Processing

As described above, one exemplary method for using windowed mass spectrometry scans to scan an entire mass range is called sequential windowed acquisition (SWATH). However, a SWATH user has to balance the number of SWATH experiments, the accumulation time, and also the number of data points across a peak.

For example, the SWATH technique provides a method to generate product ion spectra for all species detectable in a liquid chromatography coupled mass spectrometry (LCMS) analysis. This is achieved by using a wide precursor selection window that is stepped across the mass range of interest. An exemplary precursor selection window is 25 amu, but other values and even variable widths are possible. Choosing window widths and accumulation times is a balancing act with several considerations:

First, to retain liquid chromatography (LC) peak fidelity, ideally eight to ten data points per peak are needed. This defines the time that can be spent on each cycle.

Due to the nature of the method, maximum coverage of data occurs when the complete mass range is scanned. This results in a number of steps (windows) being required to cover the mass range.

To maintain a high degree of selectivity, the windows are required to be as narrow as possible, resulting in a few precursors per window. This provides less chance of fragment ion interference. This also increases the number of windows and reduces the time required for each window.

Finally, to maximize both dynamic range and sensitivity, a maximum accumulation time is required for each window.

In various embodiments, systems and methods decrease the widths of the windows in a sequential windowed acquisition while increasing the time that is spent on each window. Windows are overlapped in order to analyze each region more than once and to extract the required information post-acquisition.

Figure 2:
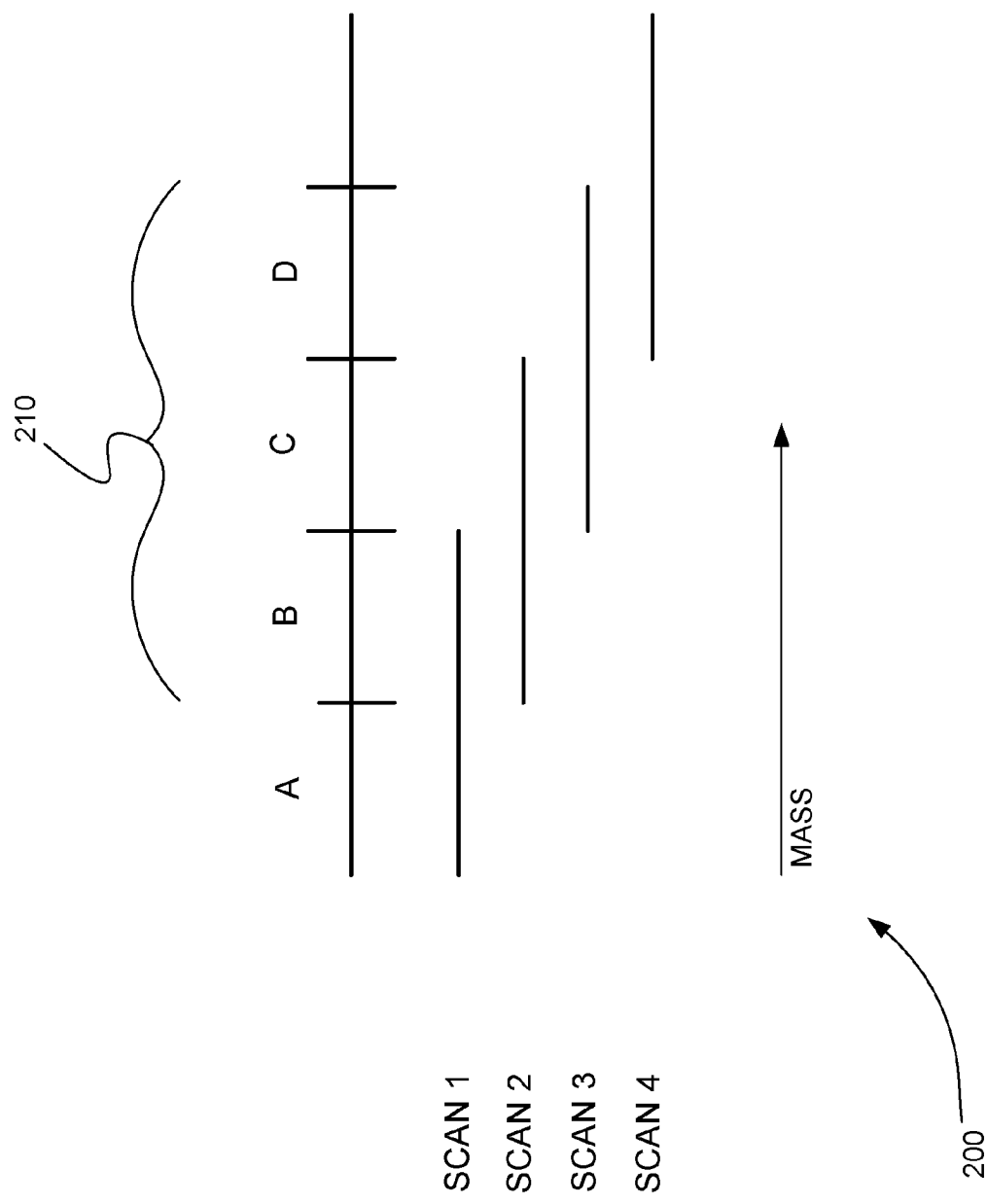
FIG. 2 is an illustration of the mass coverage of overlapping measured mass selection window widths of uniform length that are used to scan target mass selection window widths of uniform length with the same number of overlapping measured mass selection window widths, in accordance with various embodiments.

FIG. 2 is an illustration 200 of the mass coverage of overlapping measured mass selection window widths of uniform length that are used to scan target mass selection window widths of uniform length with the same number of overlapping measured mass selection window widths, in accordance with various embodiments. The mass range 210 is spanned using target mass selection window widths B, C, and D, for example. The target time per target mass selection window widths is t. Using wider measured mass selection window widths Scan 1, Scan 2, Scan 3, and Scan 4 with overlaps that correspond to the target mass selection window widths B, C, and D, the equivalent information is extracted in less time. For example, Equation 1 shows that by covering mass window C twice, the correct coverage is obtained by analyzing each window for half of the time t.

$$2C=\text{Scan 2}+\text{Scan 3}-\text{Scan 1}-\text{Scan 4} \quad (1)$$

Illustration 200 shows that measured mass selection window widths are offset by 50% of the target mass selection window width so that the effective scanning window is one half of the width actually used. In FIG. 2, each target mass selection window width is overlapped by two measured mass selection window widths. More overlap can also be provided with more or wider measured mass selection window widths, further reducing accumulation times to obtain narrower effective widths. More overlap simply increases the number of scans that are summed and subtracted to generate the desired result. This method allows wider measured windows to be used while maintaining the benefit of narrow target windows and less time to be spent on each measured window.

In FIG. 2, both the measured mass selection window widths and the target mass selection window widths have uniform widths. In various embodiments, the measured mass selection window widths, the target mass selection window widths, or both widths can be variable. In FIG. 2, the number of overlaps of measured mass selection window widths corresponding to each target mass selection window width is uniform. In various embodiments, the number of overlaps of measured mass selection window widths that correspond to target mass selection window widths can be variable. In various embodiments, any combination of measured or target window widths or number of overlaps of measured mass selection window widths can be used.

Figure 3:
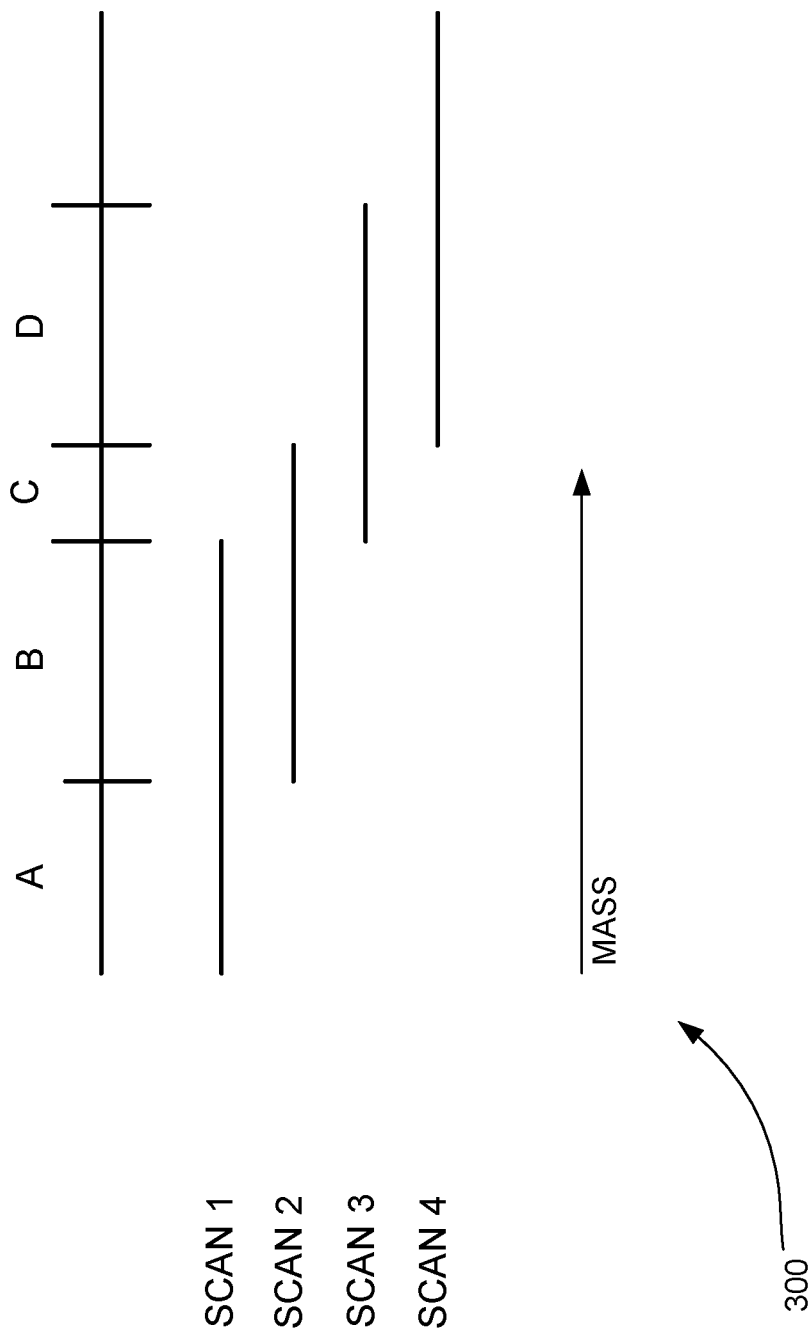
FIG. 3 is an illustration of the mass coverage of overlapping measured mass selection window widths of variable length that are used to scan target mass selection window widths of variable length with the same number of overlapping measured mass selection window widths, in accordance with various embodiments.

FIG. 3 is an illustration 300 of the mass coverage of overlapping measured mass selection window widths of variable length that are used to scan target mass selection window widths of variable length with the same number of overlapping measured mass selection window widths, in accordance with various embodiments. In FIG. 3, target mass selection window widths B and C have different widths, and measured mass selection window widths Scan 1 and Scan 2 have different widths, for example.

Figure 4:
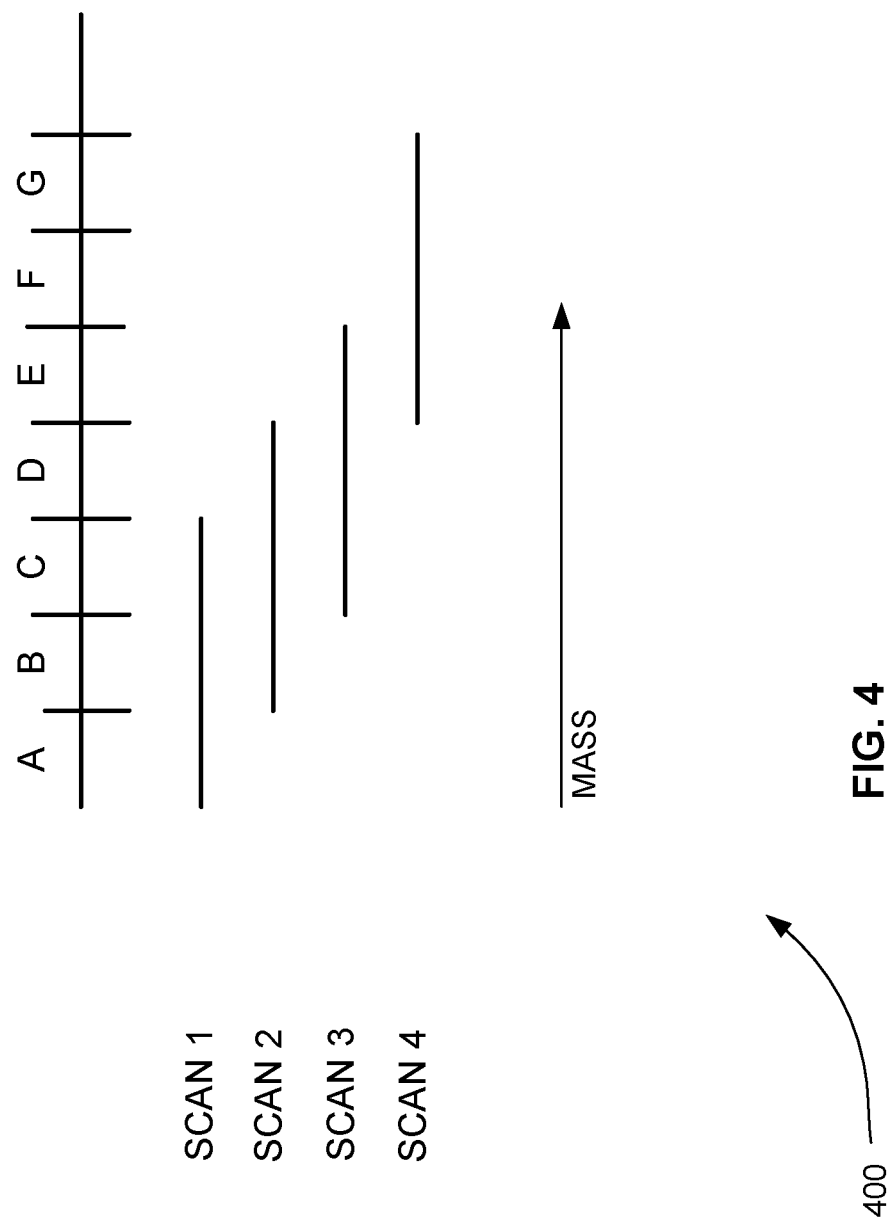
FIG. 4 is an illustration of the mass coverage of overlapping measured mass selection window widths of uniform length that are used to scan target mass selection window widths of uniform length with a variable number of overlapping measured mass selection window widths, in accordance with various embodiments.

FIG. 4 is an illustration 400 of the mass coverage of overlapping measured mass selection window widths of uniform length that are used to scan target mass selection window widths of uniform length with a variable number of overlapping measured mass selection window widths, in accordance with various embodiments. In FIG. 4, the number of overlaps of measured mass selection window widths that correspond to target mass selection window widths B and C are different, for example.

Tandem Mass Spectrometry System

Figure 5:
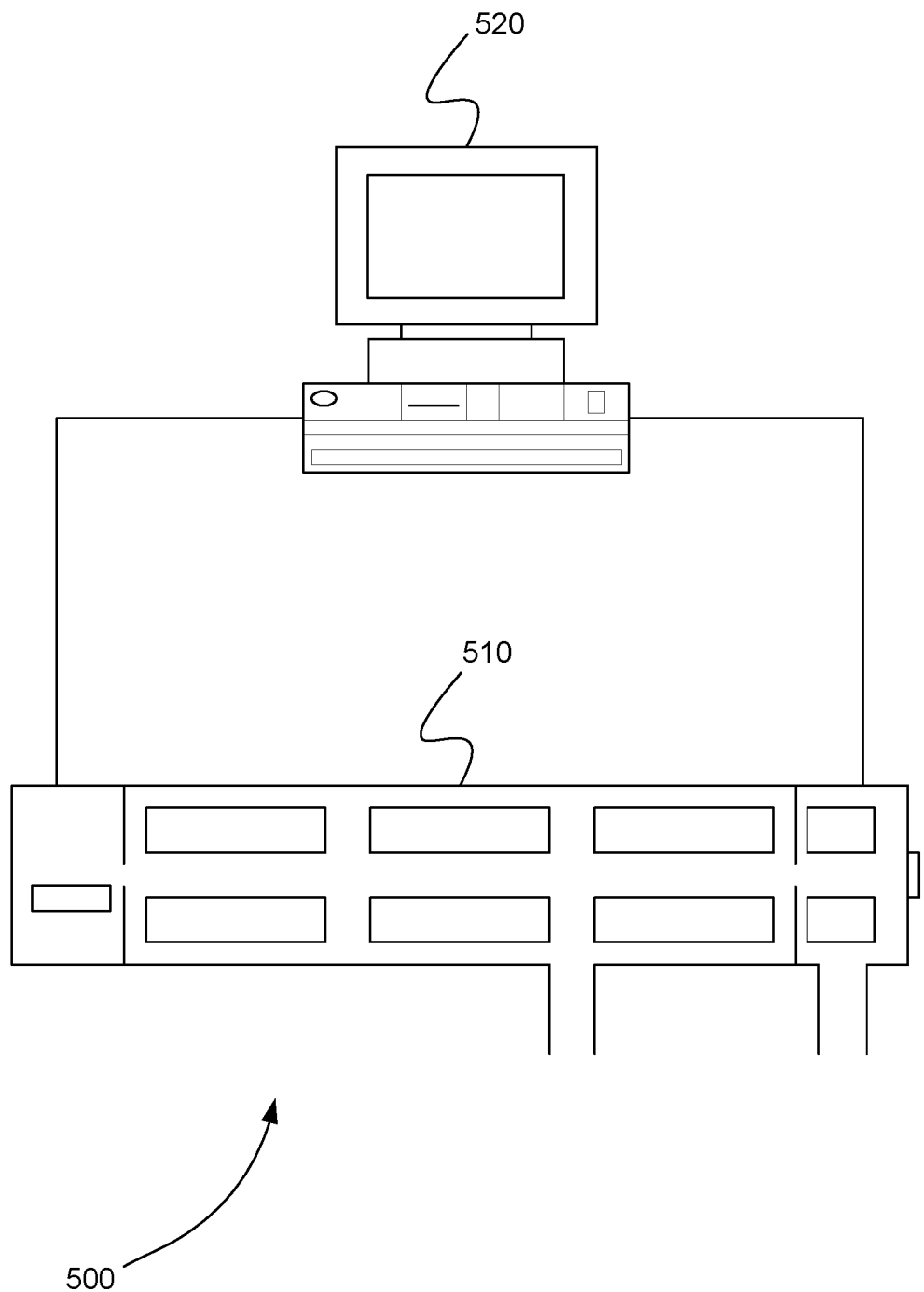
FIG. 5 is a schematic diagram showing a system for analyzing a sample using overlapping measured mass selection window widths, in accordance with various embodiments.

FIG. 5 is a schematic diagram showing a system 500 for analyzing a sample using overlapping measured mass selection window widths, in accordance with various embodiments. System 500 includes tandem mass spectrometer 510 and processor 520. Processor 520 can be, but is not limited to, a computer, microprocessor, or any device capable of sending and receiving control signals and data from mass spectrometer 510 and processing data.

Tandem mass spectrometer 510 can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, or a Fourier transform mass analyzer. Tandem mass spectrometer 510 can also include a separation device (not shown). The separation device can perform a separation technique that includes, but is not limited to, liquid chromatography, gas chromatography, capillary electrophoresis, or ion mobility. Tandem mass spectrometer 510 can include separating mass spectrometry stages or steps in space or time, respectively.

Tandem mass spectrometer 510 includes a mass analyzer that allows overlapping measured mass selection window widths.

Processor 520 is in communication with tandem mass spectrometer 510. Processor 520 divides a mass range of a sample into two or more target mass selection window widths. The two or more target mass selection window widths are based on a minimum selectivity requirement. The two or more target mass selection window widths can have the same width or variable widths.

Processor 520 instructs tandem mass spectrometer 510 to perform two or more fragmentation scans across the mass range. Each fragmentation scan of the two or more fragmentation scans has a measured mass selection window width. The two or more measured mass selection window widths of the two or more fragmentation scans can have the same width or variable widths. At least two of the two or more measured mass selection window widths overlap. The overlap in measured mass selection window widths corresponds to at least one target mass selection window width of the two or more target mass selection window widths.

In various embodiments, each target mass selection window width of the two or more target mass selection window widths corresponds to overlapped measured mass selection window widths. The number of measured mass selection window widths corresponding to target mass selection window widths can be the same or variable across the two or more target mass selection window widths.

In various embodiments, processor 520 extracts information about at least one target mass selection window width by combining information from corresponding overlapped measured mass selection window widths of at least two fragmentation scans. The information is combined using a mathematical or logical operation, for example.

Tandem Mass Spectrometry Method

Figure 6:
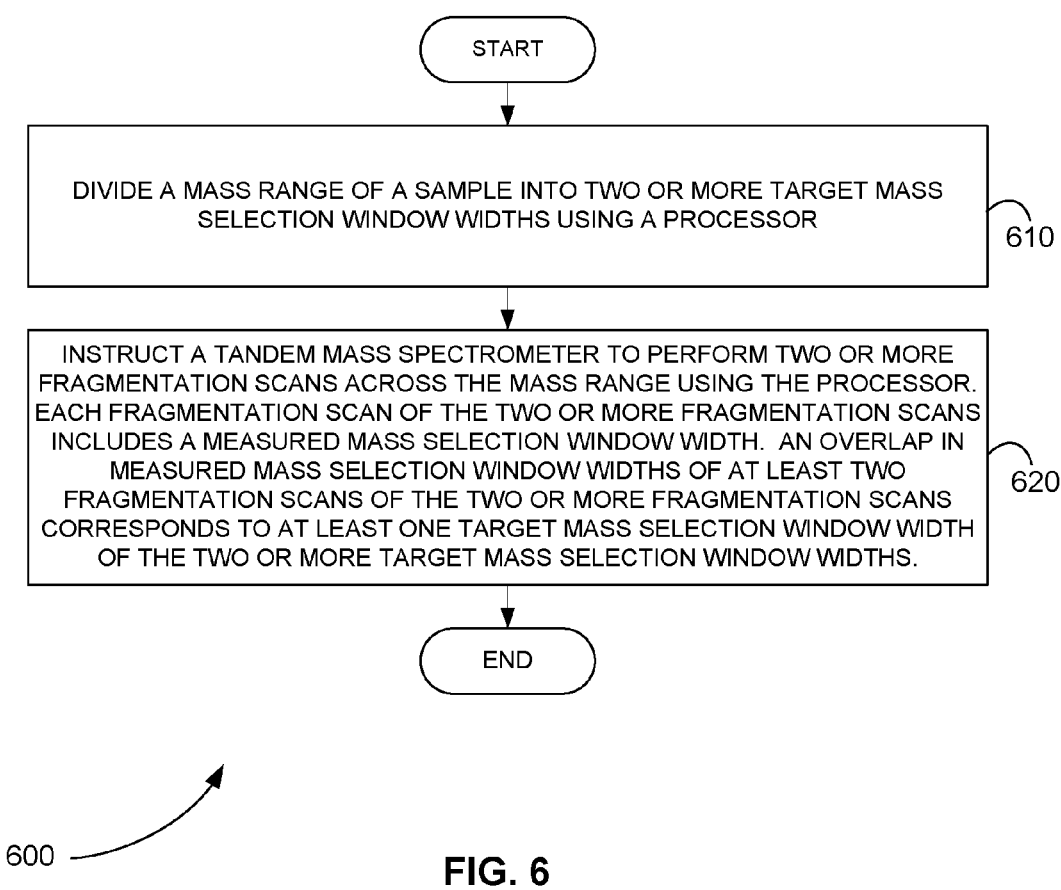
FIG. 6 is an exemplary flowchart showing a method for analyzing a sample using overlapping measured mass selection window widths, in accordance with various embodiments.

FIG. 6 is an exemplary flowchart showing a method 600 for analyzing a sample using overlapping measured mass selection window widths, in accordance with various embodiments.

In step 610 of method 600, a mass range of a sample is divided into two or more target mass selection window widths using a processor.

In step 620, a tandem mass spectrometer is instructed to perform two or more fragmentation scans across the mass range using the processor. Each fragmentation scan of the two or more fragmentation scans includes a measured mass selection window width. An overlap in measured mass selection window widths of at least two fragmentation scans of the two or more fragmentation scans corresponds to at least one target mass selection window width of the two or more target mass selection window widths.

Tandem Mass Spectrometry Computer Program Product

In various embodiments, a computer program product includes a tangible computer-readable storage medium whose contents include a program with instructions being executed on a processor so as to perform a method for analyzing a sample using overlapping measured mass selection window widths. This method is performed by a system that includes one or more distinct software modules.

Figure 7:
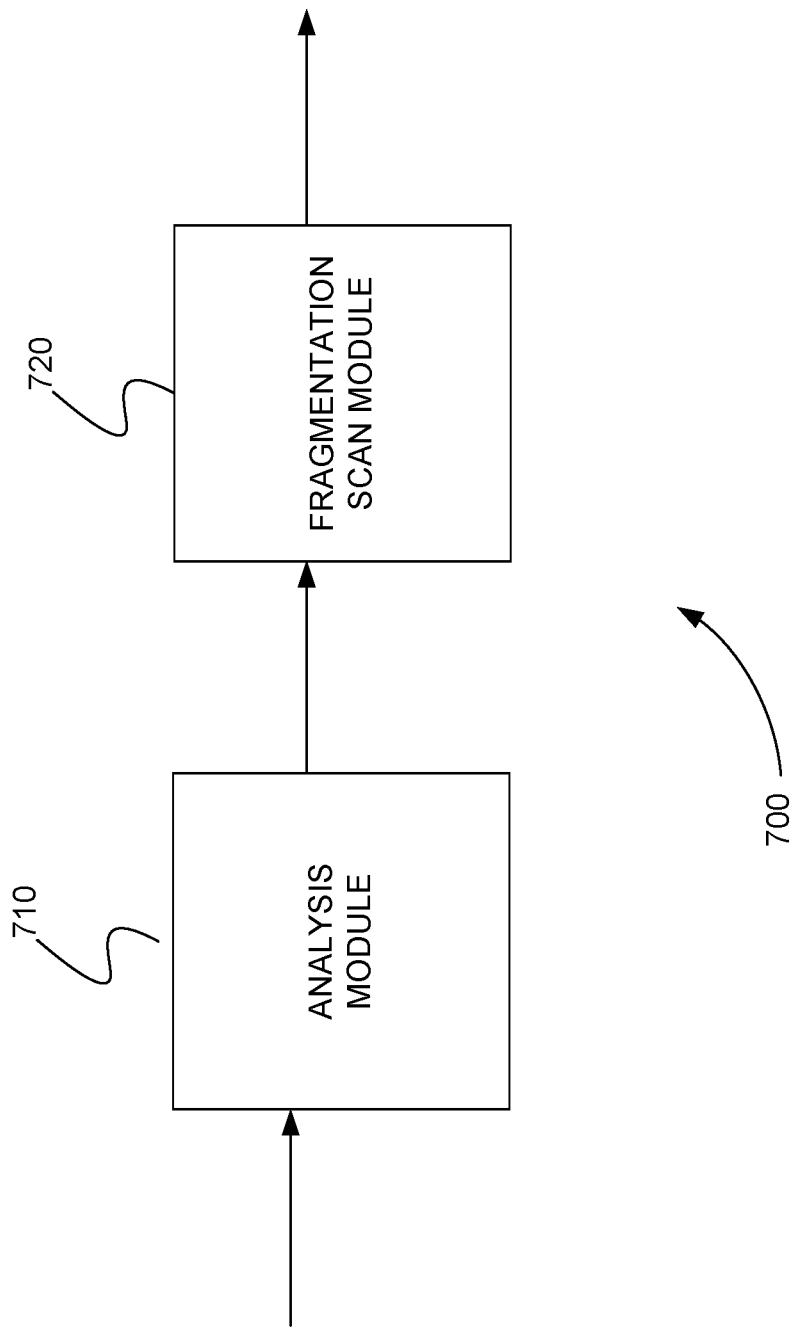
FIG. 7 is a schematic diagram of a system that includes one or more distinct software modules that performs a method for analyzing a sample using overlapping measured mass selection window widths, in accordance with various embodiments.

FIG. 7 is a schematic diagram of a system 700 that includes one or more distinct software modules that performs a method for analyzing a sample using overlapping measured mass selection window widths, in accordance with various embodiments. System 700 includes an analysis module 710 and a fragmentation scan module 720.

Analysis module 710 divides a mass range of a sample into two or more target mass selection window widths. Fragmentation scan module 720 instructs a tandem mass spectrometer to perform two or more fragmentation scans across the mass range. Each fragmentation scan of the two or more fragmentation scans includes a measured mass selection window width. An overlap in measured mass selection window widths of at least two fragmentation scans of the two or more fragmentation scans corresponds to at least one target mass selection window width of the two or more target mass selection window widths.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for analyzing a sample using overlapping measured mass selection window widths, comprising:
    a tandem mass spectrometer that includes a mass analyzer that allows overlapping measured mass selection window widths; and
    a controller in communication with the tandem mass spectrometer that is
        configured to divide a mass range of a sample into two or more target mass selection window widths, and
        configured to instruct the tandem mass spectrometer to fragment each region of the mass range at least twice using overlapping measured mass selection window widths, wherein an overlap in at least two measured mass selection window widths corresponds to at least one target mass selection window width.

2. The system of claim 1, wherein the two or more target mass selection window widths have the same width.

3. The system of claim 1, wherein the two or more target mass selection window widths have variable widths.

4. The system of claim 1, wherein the two or more measured mass selection window widths have the same width.

5. The system of claim 1, wherein the two or more measured mass selection window widths have variable widths.

6. The system of claim 1, wherein each target mass selection window width of the two or more target mass selection window widths corresponds to overlapped measured mass selection window widths that include the same number of measured mass selection window widths.

7. The system of claim 1, wherein each target mass selection window width of the two or more target mass selection window widths corresponds to overlapped measured mass selection window widths that include a variable number of measured mass selection window widths.

8. The system of claim 1, wherein the processor further extracts information about the at least one target mass selection window width by combining information from the measured mass selection window widths, wherein equivalent information is extracted in less time.

9. A system for analyzing a sample using overlapping measured mass selection window widths, comprising:
    a tandem mass spectrometer that includes a mass analyzer that allows overlapping measured mass selection window widths; and
    a processor in communication with the tandem mass spectrometer, the processor being coupled to a storage medium encoded to perform steps comprising:
        dividing a mass range of a sample into two or more target mass selection window widths, and
        instructing the tandem mass spectrometer to fragment each region of the mass range at least twice using overlapping measured mass selection window widths, wherein an overlap in at least two measured mass selection window widths corresponds to at least one target mass selection window width.

10. The system of claim 9, wherein the two or more target mass selection window widths have the same width.

11. The system of claim 9, wherein the two or more target mass selection window widths have variable widths.

12. The system of claim 9, wherein the two or more measured mass selection window widths have the same width.

13. The system of claim 9, wherein the two or more measured mass selection window widths have variable widths.

14. The system of claim 9, wherein each target mass selection window width of the two or more target mass selection window widths corresponds to overlapped measured mass selection window widths that include the same number of measured mass selection window widths.

15. The system of claim 9, wherein each target mass selection window width of the two or more target mass selection window widths corresponds to overlapped measured mass selection window widths that include a variable number of measured mass selection window widths.

16. The system of claim 9, wherein the processor further extracts information about the at least one target mass selection window width by combining information from the measured mass selection window widths, wherein equivalent information is extracted in less time.

17. A method for analyzing a sample using overlapping measured mass selection window widths, comprising:
    dividing a mass range of a sample into two or more target mass selection window widths using a processor, and
    instructing a tandem mass spectrometer to fragment each region of the mass range at least twice using overlapping measured mass selection window widths using the processor, wherein an overlap in at least two measured mass selection window widths corresponds to at least one target mass selection window width.

18. The method of claim 17, wherein the two or more target mass selection window widths have the same width.

19. The method of claim 17, wherein the two or more target mass selection window widths have variable widths.

20. The method of claim 17, wherein the two or more measured mass selection window widths have the same width.

\* \* \* \* \*